United States Patent [19]

Boyle et al.

[11] Patent Number: 4,900,660

[45] Date of Patent: Feb. 13, 1990

[54] STREPTOCOCCAL FC RC

[75] Inventors: Michael D. P. Boyle; Kathleen J. Reis; Elia M. Ayoub, all of Gainesville, Fla.

[73] Assignee: University of Florida, Gainesville, Fla.

[21] Appl. No.: 801,201

[22] Filed: Nov. 25, 1985

[51] Int. Cl.4 ...................... G01N 33/53; C07K 15/04
[52] U.S. Cl. ......................................... 435/7; 435/188; 435/885; 436/501; 436/516; 436/518; 436/519; 436/545; 436/546; 436/801; 436/819; 436/824; 436/828; 530/413; 530/810; 530/825
[58] Field of Search ........................... 435/188, 885, 7; 436/501, 516, 518, 519, 545, 546, 801, 819, 824, 828; 530/413, 810, 825

[56] References Cited

U.S. PATENT DOCUMENTS 3,966,898  6/1976  Sjöquist et al. .................... 436/828
3,995,018 11/1976  Sjöquist .................................. 435/7
4,430,318  2/1984  Langone, II ........................ 436/828

OTHER PUBLICATIONS

Reis-I J of Immunology 132 (6), pp. 3091–3097 Jun. 1984.
Langone-I J of Immunological Methods 51, 3–22(1982).
Björcik J of Immunology 133(2), pp. 969–974, 1984.
Reis-II p. 2865 in vol. 45/09-B of Diss. Abstracts International-Thesis 1983.

*Primary Examiner*—Robert J. Warden
*Assistant Examiner*—Robert Benson
*Attorney, Agent, or Firm*—Dennis P. Clarke

[57] ABSTRACT

Proteinaceous, antigenic factor derived from a group C Streptococcus which is receptor for the Fc region of IgG, a method for its preparation and immunoassay and antigen detection methods employing the receptor.

24 Claims, 7 Drawing Sheets

STREPTOCOCCAL FC RC

This application is a continuation-in-part of application Ser. No. 602,073, filed Apr. 19, 1984 now abandoned.

BACKGROUND OF THE INVENTION

There is widespread demand for proteins which bind to the Fc region of the various types of immunoglobulin G (IgG). These proteins are valuable immunochemical tools for identifying, purifying and quantifying classes and subclasses of Ig from different species. The proteins can also be used to remove IgG from serum and secretions and as immunochemical reagents in a variety of immunoassays. [Jensen, Acta Path. Microbiol. Scand., Vol. 44, p. 421 (1958); Forsgren, J. Immunol. Vol. 97, p. 822 (1966); Kronvall, J. Immunol., Vol. 111(5), p. 1401 (1973). Based on patterns of species IgG reactivity, several distinct groups of such proteins, termed Fc receptors, have been identified [Myhre et al, Immunoglobulin specificities of defined types of steptococcal Ig receptors. In: Basic Concepts of Streptococci and Steptococcal Diseases. Reedbook, Ltd., Chertsey, Surrey (eds. S. E. Holm et al), pp 209–210 (1981)].

The most extensively studied receptor is the Type I found on most *Staphylococcus aureus* strains. This receptor is presently commercially available as the so-called "Protein A". For a discussion of Protein A and its properties, see Bjork et al, Euro. J. Biochem., Vol. 29, p. 579 (1972); Kronvall, J. Scand. Immunol., Vol. 2, p. 31 (1973); Forsgren et al, Acta, Path. Microbiol. Scand., Vol. 74, p. 466 (1969); Goding, J. Immunol. Methods, Vol. 20, p. 241 (1978); Langone, J. Immunol. Methods, Vol. 51, p. 3 (1982); Kronvall et al, J. Immunol., Vol. 104, p. 140 (1970); Richman et al, J. Immunol., Vol. 28, p. 2300 (1982); Patrick et al, J. Immunol., Forsch, Vol. 153, p. 466 (1977); Lind et al, Scand. J. Immunol., Vol. 4, p. 843 (1975); Coe et al, Molec Immunol., Vol. 18, p. 1007 (1981); Ey et al, Immunochemistry, vol. 15, p. 429 (1978); Langone, Analyt. Biochem., Vol. 93, p. 207 (1979); Boyle et al, J. Natl. Can. Inst., Vol. 62, p. 1537 (1979); Langone, Methods in Enzymology, Vol. 70A (1981); Langone et al, J. Immunol. Methods, Vol. 18, p. 128 (1979); Gee et al, Analyt. Biochem., Vol. 116, p. 524 (1981); Langone, J. Immunol. Methods, Vol. 24, p. 269 (1978); Patrick et al, Immunochemistry, Vol. 15, p. 137 (1978); Langone et al, J. Immunol Methods, Vol. 18, pp. 281–293 (1977); Langone et al, Adv. Immunol., Vol. 32, p. 157 (1982). Protein A has been purified to functional homogeneity from culture supernatants and following enzyme extraction of the Protein A rich *Staphylococcus aureus* Cowan I strain. The bulk of such preparations contain a major 42,000 dalton protein and a number of other minor protein bands with Fc-reactivities. The usefulness of Protein A is limited only by the range of species, isotypes and subclasses of IgG with which it reacts.

Researchers have also successfully isolated Fc binding molecules from group A streptococcus. This receptor is heterogeneous in size, the predominantly active factor having a molecular weight of 29,500 daltons. The receptor was only obtained when protease inhibitors were included during purification. [Christensen et al, Acta. Path. Microbiol. Scand. (C), Vol. 84, p. 196 (1976); Christensen et al, Acta. Path. Microbiol. Scand. (B), Vol. 82, p. 19 (1974); Havlicek, Exp. Cell Biol., Vol. 46, p. 146 (1978); Christensen et al, Acta. Path. Microbiol. Scand. (C), Vol. 87, p. 257 (1979); Grubb et al, Int. Arch. Allergy Appl. Immunol., Vol. 67, p. 369 (1982)].

Generally, however, attempts to extract and purify streptococcal Fc receptors in any significant amounts have met with only limited success since, unlike Protein A, none of the streptococcal Fc receptors are secreted in significant quantities during culture.

The present invention is predicated on the discovery of a novel factor associated with group C streptococci which is antigenically different from both Protein A and the factor derived from group A streptococci and which selectively reacts with the Fc region of a wider variety of IgG species and subclasses than Protein A.

It is an object of the invention to provide the novel Fc binding factor and immunologically valuable derivatives thereof as well as methods for the derivation, isolation and purification thereof.

SUMMARY OF THE INVENTION

There is provided, according to the present invention, a novel, proteinaceous, antigenic factor derived from a group C streptococcus which acts as a homogenous receptor for the Fc region of various species and subclasses of mammalian IgG and which exhibits four major diffuse protein bands on polyacrylamide gel electrophoresis having apparent molecular weights of 48,000 (band I), 64,000 (band II), 90,000 (band III) and 110,000 (band IV) daltons, respectively.

The present invention also provides a method of preparing the factor comprising:

(1) solubilizing the factor from a group C streptococcus by phage lysis or trypsin extraction, (2) chromatographically separating said solubilized factor from said solution, and (3) purifying said factor by affinity chromatography on immobilized IgG.

There is also provided, according to the invention, radio-, enzyme- and electron-dense ligand-labeled factors as well as factors immobilized on inert substrates, useful as immunological reagents.

The present invention further provides an improved immunoassay method wherein a bacterial Fc receptor is reacted with a mammalian IgG to bind to a site within the Fc region thereof. The improvement comprises employing as the bacterial Fc receptor a proteinaceous, antigenic factor derived from a group C streptococcus which is a receptor for the Fc region of IgG and which exhibits four major diffuse protein bands on polyacrylamide gel electrophoresis having apparent molecular weights of 48,000 (band I), 64,000 (band II), 90,000 (band III) and 110,000 (band IV) daltons, respectively.

DETAILED DESCRIPTION OF THE INVENTION

Previously, a competitive binding assay way developed for identifying small quantities of soluble or cell surface bacterial Fc receptors [Reis et al, J. Immunol. Methods., Vol. 59, p. 83 (1983)]. Utilizing this technique Fc receptors were identified in group C streptococci. A number of extraction procedures were tested for isolating the factor, including phage lysis, hot acid an alkali extraction and treatment with a variety of enzymes including pepsin, lysostaphin, trypsin, lysozyme and mutanolysin. Soluble Fc receptor activity was observed following hot acid extraction, phage lysis or treatment of the group C streptococcus with mutanolysin. The most favorable starting material for further purification was found to result from phage lysis. This extraction procedure resulted in the highest yield of soluble Fc receptor activity while trypsin extraction resulted in the most homogeneous form of the receptor. It will be understood, however, that any extraction procedure which will result in solubilization of the factor in recoverable form without affecting the Fc binding capacity thereof may be employed.

The factor of the present invention does not occur in nature in free form, i.e., unbound to group C streptococci. The factor, isolated following phage lysis, comprises four major protein components (appearing as diffuse bands on polyacrylamide gel electrophoresis) having apparent molecular weights of 48,000; 64,000; 90,000 and 110,000 and comprising about 22%, 26%, 11% and 8% of the factor, based on the total Fc binding activity recovered following lysis of the parent group C streptococcus. Trypsin extraction resulted in a single form with a molecular weight of 30,000 daltons.

Although any group C streptococci may be employed in the method of the invention, it is preferred to utilize the strain designated 26RP66 by the Lancefield Collection, Rockefeller University, 1230 York Avenue, New York, N.Y. 10021, where the strain has been deposited inasmuch as it has been found to be extremely rich in the Fc binding factor.

The Fc receptor solubilized following phage lysis has been found to be stable for at least one month at 4° C. and for a minimum of six months at −70° C. and at no time was protease activity detectable in any extract from the 26RP66 bacteria. The Fc receptor activity is stable to hot acid, destroyed by hot alkali and destroyed by trypsin.

The specific protein in the factor responsible for Fc binding activity has not been isolated to chemical homogeniety. However, for purposes of preparing valuable immunological reagents, it is not necessary to isolate the protein. The factor isolated according to the present invention may be employed in any immunological application or other utility as if it were, in fact, the Fc binding protein itself.

The factor of the invention is preferably isolated and purified to functional homogeneity, i.e., a factor wherein the binding affinity and specificity of each of the components that comprise the Fc-receptor are identical and the mixture behaves as a single functional entity.

The functionally homogeneous Fc binding protein can be isolated according to one method by phage lysis of the bacteria and according to another method by trypsin extraction, each method being followed by sequential soluble salt [$(NH_4)_2SO_4$ sodium sulfate, polyethylene glycol, etc.] precipitation, cellulose phosphate chromatography, DEAE ion exchange chromatography and immobilized human IgG affinity chromatography described in detail hereinbelow.

All of the material recovered from the immobilized IgG column is functionally active as judged by its ability, following radioiodination, to bind to immobilized IgG. This binding was unaffected by the presence of $F(ab')_2$ fragments, indicating the receptor was binding a site on the Fc region of human IgG. The functionally active Fc receptor is physicochemically heterogeneous being resolvable into four major bands on non-denaturing polyacrylamide gels. A similar pattern with four major diffuse bands is also observed on SDS gels.

Despite the obvious heterogeneity in the size and charge of the solubilized Fc receptor it demonstrates remarkable uniformity in its binding to the Fc region of IgG. When the cold unfractionated material is used to compete with individual labeled peaks eluted from gels superimposable inhibition curves are observed with all combinations. When each of the individual unlabeled peaks eluted from non-denaturing polyacrylamide gels is tested for its ability to compete with the radiolabeled unfractionated receptor, superimposable inhibition curves are observed. These results show that for all practical purposes the affinity purified Fc receptor preparation contains a single functional activity, i.e., it binds to the same site on the Fc region of IgG with a constant affinity. An antibody prepared against the major charge species of the solubilized Fc receptor preparation is capable of totally inhibiting the functional activity of the unfractionated Fc receptor. These results suggest that the size, heterogeneity, and apparent functional homogeneity most probably result from the solubilization of a single receptor molecule covalently linked to various other cell wall constituents. Heterogeneity of this type has been observed in earlier studies attempting to isolate the M protein from streptococcal cell walls. [Fox et al, Immunochemistry 6:11–14 (1969); Kuhnemund et al, Immunobiology 159:244 (1981); Fischetti et al, J. Exp. Med. 144:32 (1976)].

The Fc receptor of the invention was recovered in a higher yield than previously reported for the factor recovered from group A streptococci. Thus, 400 $\mu$g of affinity purified group C factor/g wet weight bacteria were extracted, compared to the maximum yield previously reported of 10 $\mu$g of group A factor/g wet weight of bacteria. The heterogeneity observed was similar to that described by others. The most extensively characterized form of a streptococcal Fc receptor reported is that isolated by Grubb et al, supra, that resulted from alkaline extraction of a group A streptococcus. This receptor was isolated in a predominant 29,500 molecular weight form only when protease inhibitors were present. This receptor differs markedly from the receptor of the present invention. The smallest of the group C Fc receptors is 48,000 daltons and the functional activity was totally destroyed by treatment with hot alkali, the condition used by Grubb et al for their initial extraction. In addition, there is no evidence for protease contamination, degradation or change in heterogeneity of the group C soluble Fc receptor during purification.

The ability to isolate, in high yield, a functionally active streptococcal Fc receptor with apparent homogeneity in binding to the Fc region of IgG represents a highly useful immunochemical reagent. Staphylococcal protein A, by virtue of its selective Fc binding activity, has proved to be extremely valuable when radio or enzyme labeled as a tracer in immunoassays. [Gee et al, Anal. Biochem 116:524 (1981); Langone, J. Immunol. Methods 24:263 (1978); Langone, J. Immunol. Methods 51:3 (1982)]. In addition, immobilized protein A has been used for isolation of various classes and subclasses of IgG [Ey et al, Immunochem 15:429 (1978); Patrick et al, Immunochem. 15:137 (1978)], separation of antigen-antibody complexes [Kessler et al, J. Immunol 117:1482 (1976); MacSween et al, J. Immunol. Methods 23:259 (1978)] or for selective removal of IgG from serum [Boyle et al, J. Immunol Methods 32:51 (1980); Langone et al, Analyt. Biochem 93:207 (1979); Goding, J. Immunol. Methods 20:241 (1978)]. The Fc receptor of the present invention has species or subclass reactivities different from staphylococcal protein A and is therefore highly useful as expanding the immunochemical approaches currently using Protein A.

The ion exchange chromatographic step for separating the solubilized factor from the extraction solution is preferably carried out in a diethylaminoethyl cellulose column. It will be understood, however, that any suitable anion-exchange material may be employed (e.g., Whatman 52 DEAE, DEAE sephadex, Dowex-50 or equivalent thereof).

The factor may be eluted from the column with a 0.14 M to 0.18 M soluble salt solution The affinity chromatography step is preferably conducted according to the method outlined in U.S Pat. No. 3,850,798, i e , employing human IgG covalently immobilized on any suitable inert substrate, e.g., of Afi-gel 10, Afi-gel 15, cyanogen bromide activated sepharose, etc. It will be understood, however, that any species of IgG, including goat, rabbit, cow, pig, etc. to which the factor binds may be employed.

The phage lysis may be carried out utilizing any suitable bacteriophage (i.e., any phage that will infect group C streptococci such as 21 597-B1 in the American type culture collection) in any amount of from about $5 \times 10^{11}$ to about $1 \times 10^{13}$ plaque forming units of phage per liter of culture.

The invention is illustrated by the following non-limiting examples wherein the following abbreviations and definitions apply:

PBS—0.15M phosphate buffered saline, pH 7.4; PA—Staphylococcal protein A; FcR—Receptor for the Fc region of IgG; FcRc—Affinity purified streptococcal Fc receptor factor from the group C streptococcus 26RP66; VBS-gel—veronal buffered saline, pH 7.4, containing 0.001 M $Mg^{2+}$ and 0.0015 M $Ca^{2+}$ and 0.1% gelatin; EDTA-gel, isotonic veronal buffered saline, pH 7.4, containing 0.01M ethylendiamine-tetraacetate (EDTA) and 0.1% gelatin; S.D.S.—sodium dodecyl sulfate, PAGE—polyacrylamide gel elecrophoresis.

The β-hemolytic group C streptococcal strain designated 26RP66 and the C1 bacteriophage were obtained from Rockefeller University, New York, N.Y. This strain was selected based on its high surface Fc-receptor activity as determined by immunoassay as described by Reis et al, J. Immunol. Methods 59:83 (1983). For all of the studies bacteria were grown in Todd Hewitt broth and phage lysis was carried out using a modification of the procedure of Fischetti et al, J. Exp. Med. 133, 1105 (1971).

Phage-associated lysin activity was detected by the lysis of a group A streptococcal strain as described by Fischetti et al, ibid.

EXAMPLE 1

Extraction of Fc-receptors

The streptococcal strain 26RP66 was grown overnight in 3 Liters of Todd Hewitt broth. A bacterial pellet was recovered by centrifugation and washed once in phosphate buffer saline (PBS) pH 7.4. Aliquots containing approximately 0.25 g of bacteria (wet weight) were enzyme extracted into 6 ml of appropriate buffer containing 100 μg DNAse under the following conditions.

(1) Mutanolysin (Miles) extraction was carried out using 2,000 units of enzyme in 0.05M $KH_2PO_4$, pH 6.5 [Siegel et al, Infect. Immunol. 31:808 (1981)].

(2) Pepsin (Sigma) extraction was carried out using 1,750 units in 0.05 M $KH_2PO_4$, pH 5.8 [Manjula et al, J. Immunol. 124:26 (1980)].

(3) Lysozyme (Sigma) extraction was carried out using 24,000 units in 0.05 M $KH_2PO_4$, pH 6.3 [Forsgren, Acta. Path. Microbiol. Scand. 75:481 (1969)].

(4) Lysostaphin (Sigma) extraction was carried out using 175 units in 0.05 M Tris-HC1, 0.15 M NaCl, pH 7.5 [Sjoquist et al, Eur. J. Biochem. 29:5721].

(5) Phage lysis utilizing $5 \times 10^{11}$ to $1 \times 10^{13}$ plaque forming units of 21597-B1 (ATCC).

(6) Trypsin extraction was carried out by incubating 3 g wet weight of bacteria with 10 μg/ml trypsin in total volume of 75 ml of 0.05 M $KH_2PO_4$, 0.005M EDTA, pH 6.1 for 1.5 hours at 37° C.

All extractions were carried out for 4 hours at 37° C. The extracts were then centrifuged at 10,000 g for 15 minutes and the supernatants recovered, dialyzed against PBS, and stored at 4° C. until tested for functional FcRc activity by the method described below. Detergent extraction was carried out in a similar way using 1% Tween-20 in 0.15 M PBS, pH 7 4.

Hot acid/hot alkaline extracts were carried out according to the method of Lancefield [J. Exp. Med. 47:91 (1928)]. Bacteria, 0.25 g wet weight were suspended in 3 ml of 0.15 M PBS and the pH was adjusted to 2.0 (or 10) with 0.5 M HCl (or 0.5 M NaOH). The bacterial suspension was boiled for 10 minutes and the pH was neutralized. The final volume was adjusted to 6.0 ml and the supernatants recovered as described above.

The method employed for the detection of soluble Fc receptors in the extracts is described by Reis, J. Immunol. Methods 59:83 (1983). Essentially, this competitive binding assay measures the ability of Fc receptors to inhibit binding of either $^{125}I$ labeled protein A or $^{125}I$ labeled Fc receptor to immobilized human or rabbit IgG. Initially, $^{125}I$ protein A was used and one unit of Fc receptor activity was defined as the concentration of material that would inhibit its binding by 30% under standard assay conditions. Thirty percent inhibition was chosen because it was in a linear proportion of the inhibition curve and activity in fractionated samples could be detected without prior concentration. Once streptococcal Fc receptors had been isolated and labeled, they were used for the assay and an absolute value in ng/ml was assigned based on the inhibition of affinity purified standards included in each assay. The absolute protein concentration of the standard was determined using the Bio-Rad protein assay (Richmond, Calif.), which is a modification of Bradford's method.

Of the variety of extraction procedures tested, including phage lysis, alkaline extraction, acid extraction, detergent extraction, enzyme treatment with pepsin, lysostaphin, lysozyme or mutanolysin, the only treatments that resulted in significant quantities of soluble Fc receptor activity were phage lysis (approximately $5 \times 10^4$ units/g bacteria extracted), mutanolysin treatment (approximately $3 \times 10^4$ units/g bacteria extracted) and treatment with hot acid (approximately $2 \times 10^4$ units/g bacteria extracted). Extraction of the bacteria with detergent, hot alkali, lysozyme or lysostaphin did not solubilize detectable quantities of a functionally active Fc receptor. The extracts were compared by three criteria: (1) the total yield of Fc receptor recovered/unit weight of bacteria, (2) the specific activity calculated as the soluble FcR activity divided by the $OD_{280}$ of the extract and (3) the charge heterogeneity of functional activity. This was measured following elution from non-denaturing polyacrylamide gels as described below. The material obtained by phage lysis of bacteria demonstrated the highest yield, highest specific activity. The trypsin extracted material was among the least heterogeneous of the extracts.

Phage Lysis

The group C streptococcus was grown to an $OD_{650}$ of 0.3 in Todd Hewitt broth. To this culture was added approximately $3 \times 10^{12}$ pfu of Cl bacteriophage/liter of culture and the bacteria allowed to lyse. After lysis was complete EDTA was added to a final concentration of 0.05 M and DNase to a final concentration of 0.5 μg/ml. The resulting supernatant was filtered through a sinter glass filter and shown to contain two soluble activities: (1) an Fc receptor activity and (2) a bacteriolytic enzyme activity - the phage associated lysin originally described by Fischetti et al, supra. The supernatant contained no detectable protease activity and the Fc receptor activity was found to be stable for over a month at 4° C. or in excess of six months at −70° C. The crude supernatant was concentrated 30 fold using a Millipore Pellicon concentrator with a molecular weight cut-off of 10,000 daltons. Residual cellular debris was removed by centrifugation at 27,000 g for 2 hours and the resulting supernatant was precipitated by adjusting to 50% saturation with $(NH_4)_2SO_4$. The precipitate was recovered by sedimentation at 27,000 g for 2 hour at 4° C. and then resuspended in a minimal volume of 0.5 M phosphate buffer pH 6.1 containing 0.005 M EDTA. This material was dialyzed against the same buffer and then ultra-centrifuged at 90,000 g for 5 hours at 4° C. The soluble supernatant contained both the Fc-receptor activity and the phage associated lysin activity and was subjected to further purification.

Trypsin Extraction

The streptococcal strain 26RP66 was grown overnight in stationary cultures containing 3 liters of Todd Hewitt broth. A bacterial pellet was recovered by centrifugation and washed once in phosphate buffer saline (PBS) pH 7.4. Aliquots containing approximately 3–7 g of bacteria (wet weight) were enzyme extracted into 25–75 ml of appropriate buffer containing 25 μg DNAse under the following conditions:

Trypsin extraction was carried out initially by incubating 3 g wet weight of bacteria with 10 μg/ml trypsin in a total volume of 75 ml of 0.05 M $KH_2PO_4$ containing 0.005 M EDTA, pH 6.1, for 1.5 hours at 37° C. The trypsin extraction conditions can be modified to obtain the most homogeneous product. Trypsin was inactivated by the addition of soybean trypsin inhibitor (Millipore Corp., Freehold, N.J.) or by the addition of benzamidine. Unlysed bacteria were removed by centrifugation at 10,000 g for 15 minutes and the supernatant was stored at 4° C. until tested for Fc receptor activity.

Experiments were carried out using a fixed concentration of bacteria (0.25 μg wet weight) suspended in a total volume of 2.5 ml of 0.5 M $KH_2PO_4$, 0.005 M EDTA, pH 6.1, and incubating with 20 μg/ml trypsin for varying times at 37° C. At the end of the incubation period benzamidine was added to the reaction mixture to a final concentration of 100 mM to prevent further trypsin activity and the cell free supernatants harvested. Samples of bacteria incubated under these conditions without added trypsin were also harvested. The total extracted material was tested for total extractable Fc receptor, for extracted protein and for heterogeneity of Fc receptors extracted. These results demonstrated that trypsin rapidly solubilized Fc receptor from the bacteria, and that at early time points (15–20 minutes) a single functionally active Fc receptor was observed. This receptor had a molecular weight of 30,000. Prolonged trypsin treatment resulted in the appearance of a second receptor with a molecular weight of 24,000 daltons. The trypsin treatment did not result in the solubilization of large quantities of cell surface proteins as can be seen in a silver stained gel of the extracted material. This suggested that brief trypsinization (15–20 minutes at 37° C.) of the streptococci under the conditions described would yield a homogeneous Fc receptor. Trypsinization for longer periods (>3 hours) resulted in the appearance of a second Fc receptor activity at a lower molecular weight and with a slightly lower yield and specific activity of product. Treatment with trypsin for more than 6 hours completely destroyed the Fc receptor binding activity.

These results suggest that a homogeneous Fc receptor could be extracted employing appropriate conditions for trypsin treatment (e.g., 1.5 hours at 37° C. in 0.05M $KH_2PO_4$, 0.005M EDTA, pH 6.1.)

EXAMPLE 2

Purification of the Factor

Previously, Fischetti et al, supra, had defined conditions under which the phage-associated lysin binds to cellulose phosphate. Using these conditions, 20 ml of the crude phage lysate was applied to a $1.5 \times 16$ cm cellulose phosphate (Whatman P11) column which was equilibrated with 0.1 M $KH_2PO_4$, pH 6.1, containing 0.005 M EDTA and 10% glycerol. Once the $OD_{280}$ had returned to base line, the column was eluted with the same buffer containing 0.4 NaCl. In agreement with the findings of Fischetti et al, the phage-associated enzyme was eluted from the cellulose phosphate under these conditions. Aliquots of the fractions collected were tested for Fc receptor activity and 98% of the total recovered activity and 95% of the total recovered $OD_{280}$ passed directly through the column.

The phage associated lysin can be stabilized and stored as described by Fischetti et al, supra, although the cellulose phosphate step does not result in any significant purification of the Fc receptor. It is to be understood, however, that the products and methods of the invention include the factors containing phage associated lysin as well as factors from which the lysin is removed.

In the next step of the purification procedure all fractions containing Fc receptor activity from the cellulose phosphate, flow through material were dialyzed against 0.015 M NaCl and applied to a diethylaminoethyl cellulose (DEAE) column equilibrated in 0.015 M NaCl, pH 7.4, and unbound material was eluted in 0.015 M NaCl. Once the $OD_{280}$ had returned to base line values a linear gradient of NaCl from 0.05–0.5 M was applied, and finally, the column was eluted with 1.5 M NaCl. The NaCl concentration was followed in the collected fractions by measuring conductivity and the soluble FcRc activity was monitored using the competitive binding assay described below. The majority of the Fc receptor activity was recovered in a single peak (peak I) which was eluted between a NaCl concentration of 0.12 and 0.18 M (see FIG. 1). A second peak (peak II) containing approximately 5% of the recovered activity was obtained at a NaCl concentration close to 0.24 M.

Immobilized IgG for affinity purification of the streptococcal Fc receptor was prepared by covalently coupling human IgG to the high capacity Afi-gel 15 activated beads (Bio-Rad, Richmond, Calif.). Ten milligrams of gel washed with 3 volumes of isopropanol and 3 volumes of deionized water was mixed with 10 ml of human IgG containing 7.3 mg IgG/ml The coupling reaction was carried out in 0.1 M HEPES, pH 7.5 at 4° C. overnight with gentle rocking. Unreacted sites were blocked by the addition of 0.1 ml of 1 M ethanolamine HCl, pH 8.0 for each ml of gel. One hour was allowed for complete blocking and the IgG coupled gel was extensively washed in VBS gel and stored in 4° C. in VBS gel containing 0.02% sodium azide. Prior to use the immobilized IgG was washed with 10 volumes of glycine-HCl, pH 2.0 and reequilibrated in phosphate buffered saline, pH 7.4.

Fractions containing Fc receptor activity from the DEAE peak I were pooled and concentrated by Amicon ultra-filtration using a PM10 (molecular weight cut-off of 10,000) and further purified by applying to a column of human IgG immobilized on Afi-gel 15. The column was washed with 0.15 M PBS, pH 7.4 to remove unbound material and the bound Fc receptor was eluted from the column using 0.1 M glycine-HCl, pH 2.0. The eluted fractions were dialyzed against PBS, pH 7.4 and tested for functional Fc receptor activity and protein content. The resulting product contained 5,334 Fc receptor units/ml and 58 µg/ml of protein. There was no detectable sugar as measured by the phenol sulphuric acid method [Dubois et al, Anal. Chem. 28:350 (1956)]. The overall purification achieved by this procedure is summarized in Table 1.

al, Immunochemistry 8:289 (1971). The labeled protein was separated from free iodine by passage over a G25 column (PL-10, Pharmacia) and collected in veronal buffered saline, pH 7.4, containing 0.001 M $Mg^{2+}$, and 0.1% gelatin (VBS-gel). The labeled protein A and Fc-receptor were routinely found to have specific activities of approximately 0.25 mCi/mg.

FcRc preparations containing 15–60 µg of unlabeled material or $1.7 \times 10^5$ cpm of iodinated material were applied to 7% polyacrylamide disc gels. Samples were electrophoresed at 1.5 mamp per gel in 0.025 M Tris, 0.2 M glycine, pH 8.3 until the tracking dye was 2 cm from the bottom of the gel. Gels were either fixed and stained with Coomassie Brilliant Blue or frozen and sliced into 1 mm sections. Gel slices were either counted for radioactivity on an LKB gamma counter or eluted for 72 hours into VBS-gel to determine functional activity. Samples were also run on 0.1% SDS, 7% polyacrylamide gels as described above with two exceptions. First, all samples were boiled for 1 minute in 2% SDS prior to electrophoresis. Second, the electrophoresis buffer was 0.1% SDS, 0.025 M Tris 0.2 M glycine pH 8.3. Molecular Weight Standards (Sigma, St. Louis) were included in each SDS polyacrylamide gel assay. Myosin (200,000 daltons), β-galactosidase (116,000 daltons), phosphorylase b (94,000 daltons), bovine serum albumin (68,000 daltons), egg albumin (43,000 daltons), carbonic anhydrase (30,000 daltons) and β-lactoglobin (18, 400 daltons)

Antibody to the streptococcal FcRc was prepared by immunizing white leghorn hens using the following schedule. Pre-immunization samples were obtained two days prior to the initial injection. Chickens were injected with 25 µg of FcRc intramuscularly (I.M.) in complete Freund's adjuvant. Blood samples were ob-

TABLE 1

Purification of a Group C Streptococcal Fc Receptor[a] Factor

| Fraction | Vol m. | FcR units/ ml | FcR Recovery Percent | $OD_{280}$/ ml | $OD_{280}$ Recovery Percent | Specific Activity FcR units/$OD_{280}$ | Purification |
|---|---|---|---|---|---|---|---|
| Crude[b] Lysate | 115 | 9720 | 100 | 30.4 | 100 | 320 | 1 |
| Cellulose Phosphate | 560 | 1302 | 65 | 4.3 | 69 | 302 | 0.9 |
| DEAE | 170 | 3876 | 60 | 2.0 | 10 | 1,967 | 6 |
| Immobilized IgG | 66 | 5334 | 32 | 0.10 | 0.2 | 53,340 | 167 |

[a]One unit of Fc receptor activity is the concentration of material required to inhibit the binding of $^{125}I$ protein A by 30% in the competitive binding assay.
[b]The crude lysate refers to the cell free 50% $(NH_2)SO_4$ pellet resuspended in 0.5 M phosphate buffer, pH 6.1, containing 0.005 M EDTA.

EXAMPLE 3

Functional and Chemical Purity of the Factor

Stock human IgG was prepared by chromatography of normal human serum on DEAE cellulose [Boyle et al, J. Immunol. Methods 32:51 (1980)]. Aliquots were stored at −70° C. until use. F(ab)$_2$ fragments of human IgG were prepared by pepsin digestion as described by Reis et al, J. Immunol. Methods 59:83 (1983). IgG was immobilized to Immunobeads (Bio Rad, Richmond, Calif.) for use in the competitive binding assay as described by Langone et al, J. Immunol. Methods 18:281 (1977).

Purified PA was obtained from Pharmacia Fine Chemicals, Piscataway, N.J.

Purified RA and the streptococcal Fc-receptor were iodinated by the mild lactoperoxidase method using enzyme beads (Bio-Rad) by the method of Morrison et tained two weeks later to test for antibody production. Two weeks and five weeks after the initial injection, the chickens were boosted with I.M. with 25 µg of FcRc in incomplete Freund's adjuvant. Serum was collected one week after the final injection.

Antibodies to streptococcal FcRc were measured by the following method: In this assay the antigen combining sites on chicken anti-FcRc antibody compete with the Fc region of human IgG immobilized on agarose beads (Bio-Rad) for radio iodinated FcRc. Antiserum to FcRc was diluted in veronal buffered saline pH 7.4, containing 0.1% gelatin (VBS-gel) and 0.2 ml of the dilution was mixed with 0.1 of a standard suspension of immobilized human IgG beads and 0.1 ml of iodinated FcRc containing approximately 30,000 cpm. Following a 1.5 hr. incubation at 37° C., 2 ml of EDTA-gel was added to each tube. The tubes were centrifuged at 1,000 g for 5 min. and the supernatant fluid decanted. Following a second wash with an additional 2 ml of EDTA-gel, the amount of $^{125}$I FcRc adhering to the beads was determined in an LKB Gamma Counter. Maximal binding of $^{125}$I FcRc to the Immunobeads was approximately 6,000 cpm. The number of counts recovered when the assay was performed without Immunobeads present (i.e., the background) was approximately 200 cpm. By comparing the number of counts bound in the absence of chicken anti-FcRc to the number of counts bound to the beads in the presence of various dilutions of chicken anti-FcRc, the degree of inhibition of FcRc binding can be calculated and a standard curve relating antibody concentration to inhibition is obtained. No inhibition of binding of $^{125}$I FcRc was observed in the presence of pre-immunization chicken serum.

The affinity purified Fc receptor was concentrated 10 fold by Amicon Ultrafiltration using a PM-membrane. One hundred microliters of this material, containing approximately $5 \times 10^3$ Fc receptor units and 58 μg of protein, was iodinated using the Immunobead reagent. When an aliquot of the iodinated affinity purified Fc receptor was mixed with immobilized human IgG, 96% of the radioactivity could be removed by two adsorptions. This adsorption was not inhibited by the addition of human IgG F(ab')$_2$ fragments derived from the same isolated IgG pool used to prepare the immobilized human IgG beads. These results demonstrate that the recovered affinity purified Fc receptor was functionally active and that binding was directed against the Fc region of IgG. Treatment of the labeled Fc receptor with excess trypsin resulted in loss of binding activity further indicating the protein nature of the receptor.

Fifty-eight micrograms of unlabeled affinity purified Fc receptor was applied to duplicate 7% non-denaturing polyacrylamide disc gels. One gel was stained with Coomassie blue while the second gel was sliced and eluted into 0.15 M VBS-gel pH 7.4 for 72 hours. The functional activity in the eluted samples was measured using the competitive binding assay described above. The results presented in FIG. 2B demonstrate that four major protein bands were detected by staining and these bands correspond to the functional Fc receptor activity. A similar pattern was observed when radiolabeled Fc receptor was applied to gels and the distribution of $^{125}$I monitored. See FIG. 3 The distribution of counts indicated that band I contained 22%, band II (the major stained band) contained 26%, band III contained 11% and band IV contained 8% of the labeled Fc receptor material, respectively. The remainder of the counts were dispersed at low levels throughout the gel (FIG. 3). The crude lysate electrophoresed under similar conditions demonstrated a similar pattern of functional activity indicating that the four peaks did not develop during the purification procedure (FIG. 2A).

Four major diffuse bands were also observed on SDS gels with molecular weights of 110,000, 90,000, 64,000 and 48,000, respectively. The predominant stained protein species was the 64,000 molecular weight protein.

To determine whether the observed heterogeneity of Fc receptor activity represented distinct receptors or a common receptor with differing cell wall constituents covalently linked, two approaches were used. In the first, each of the active fractions of radiolabeled Fc receptor recovered by elution from non-denaturing polyacrylamide gels was tested for its ability to be inhibited from binding to immobilized human IgG by various concentrations of unfractionated unlabeled Fc receptor in the competitive binding assay. The results shown in FIG. 4 demonstrate superimposable inhibition curves for each fraction and suggest that the Fc receptor activity in each peak was directed against a similar site on the Fc region of the immobilized human IgG and that each receptor demonstrated a similar affinity.

The second approach to study the interrelationship of the four charged species of functionally active Fc receptor was to prepare antibody to the major Fc receptor activity. The affinity purified Fc receptor was separated by electrophoresis on a series of non-denaturing polyacrylamide gels. Each gel was stained and the region of the gel containing the major stained protein band was cut out, emulsified in complete Freund's adjuvant and injected into chicken following the immunization schedule described above. The production of antibody was followed by the ability of the immune chicken serum to inhibit binding of $^{125}$I Fc receptor to immobilized human IgG beads. The results shown in FIG. 5 demonstrate that the resulting antibody could completely inhibit binding of the $^{125}$I labeled unfractionated Fc receptor to immobilized human IgG. Chicken serum obtained prior to immunization was without effect. The labeled tracer contains all four major charge species of Fc receptor (see FIG. 3) and the antibody was prepared only against the second peak which contains 26% of the total Fc receptor activity. These findings suggest that each of the four peaks in the affinity purified Fc receptor preparation contains antigenically related structures. Taken together the results in FIGS. 4 and 5 suggest that the group C streptococcus has a single functional Fc receptor that is extracted with differing cell wall fragments that account for the heterogeneity observed on non-denaturing and SDS polyacrylamide gels.

The factors (i.e., isolated by phage lysis or trypsin extraction) may be labeled with any suitable radioisotope (e.g., $^{125}$I, $^{131}$I, $^3$H, $^{14}$C, $^{35}$S, etc.), enzyme (e.g., lactoperoxidase, horse-radish peroxidase, etc.) or a fluorescent tag (e.g., fluoroscein isothiocyanate, rhodamine, etc., and, if desired, immobilized to a suitable inert support for use as an immuno-reagent. Methods for producing such labeled proteins are well known to those skilled in the art. [See, e.g., *Methods in Enzymology*, Vols. 70, 74 and 92, Ed. Langone, T. T., Van Vunakis 7, 1983, Academic Press.]

EXAMPLE 4

Comparison of FcRc Factor With Protein A

Soluble streptococcal Fc receptor (FcRc) was isolated and purified to functional homogeneity from a group C strain designated 26RP66 as described above.

Purified PA was obtained from Pharmacia Fine Chemicals, Piscataway, N.J.

The affinity purified FcRc was separated by electrophoresis into four functionally active fractions on 7% non-denaturing polyacrylamide gels as described above.

Purified protein A (Pharmacia) and the affinity purified FcRc were iodinated by the mild lactoperoxidase method using enzyme beads (Bio-Rad) as described above.

Protein A and FcRc were quantified using a modification of the competitive binding assay of Langone et al, J. Immunol Meth. 18:281 (1977)]. In this assay 0.2 ml of a test sample of buffer is mixed with 0.2 ml of a standard suspension of agarose beads with covalently coupled human, rabbit or goat IgG (Bio-Rad Laboratories, Richmond, Calif.), and 0.1 ml of $^{125}I$ protein A or $^{125}I$ FcRc (approximately 20,000 cpm) and incubated at 37° C. for 90 min. Two milliliters of veronal buffered saline containing 0.01M trisodium ethylenediaminetetraacetate and 0.1% gelatin (EDTA-gel) was added to each tube and centrifuged at 1,000 g for 5 min. and the supernatant fluid decanted. After an additional wash, the radioactivity associated with the beads was determined in an LKB Gamma Counter. The number of counts bound in the absence of fluid phase PA or FcRc was compared to the number of counts bound to the beads in the presence of known amounts of fluid phase PA or FcRc and the degree of inhibition determined. The functional activity of these two receptors was compared by competing unlabeled PA or FcRc with either $^{125}I$-PA or $^{125}I$-FcRc.

Human IgG was coupled to immunobeads (Bio-Rad) for use in the competitive binding assays as described above. Rabbit and goat IgG covalently coupled to immunobeads (Immonobead R-1 and Immunobead G-1, respectively) were obtained from Bio-Rad, Richmond, Calif.

Monospecific antiserum to staphylococcal protein A was obtained from the National Cancer Institute, Bethesda, Md. The antiserum was prepared as described above. Monospecific antiserum to streptococcal FcRc was prepared as described above.

IgG from a variety of species was quantified by a competetive binding assay developed by Langone et al, supra, and modified as described by Reis et al, J. Immunol. Methods 59:85 (1983). The ability of different species IgG's to inhibit the binding of either $^{125}I$-PA or $^{125}I$-FcRc to immobilized human IgG was compared.

Stock human IgG was prepared by chromatography of normal human serum on DEAE cellulose according to the method of Boyle et al, J. Immunol. Methods 32:51 (1980). Aliquots were stored at −70° C. until use. Purified rabbit, cow, sheep, goat, rat, dog and pig IgG were obtained from Cappel Laboratories, Inc., Cochranville, Pa.

Human IgG subclasses were provided by the WHO/IUIS Immunoglobulin Subcommittee. Two samples of each subclass were tested:

IgG$_1$ (k) lot #0781 and IgG$_1$ (λ) lot #0180
IgG$_2$ (k) lot #0380 and IgG$_2$ (λ) lot #0981
IgG$_3$ (k) lot #0282 and IgG$_3$ (λ) lot #0381
IgG$_4$ (k) lot #0981 and IgG$_4$ (λ) lot #0880.

Inhibition of Binding of $^{125}I$ PA or $^{125}I$ FcRc to Immobilized Human IgG by Unlabeled PA or FcRc As shown above, the isolated functionally active FcRc is composed of four major charges species that can be readily separated and recovered following electrophoresis and elution from non-denaturing polyacrylamide gels. Each fraction eluted from the gel has been shown to bind the Fc-region of IgG and all are antigenically related.

By comparing the inhibition of binding to labeled tracer to immobilized IgG by (1) unlabeled protein A, (2) unlabeled affinity purified FcRc or, (3) affinity purified FcRc that was further fractionated on polyacrylamide gels, the results shown in FIG. 6A demonstrate that binding of $^{125}$ PA could be inhibited by any of the FcRc fractions tested and that each FcRc fraction showed a superimposable inhibition curve. These results indicate that the binding site on the Fc-region of human IgG for protein A and FcRc are either identical or in close proximity. When the experiment was repeated using $^{125}I$ FcRc as tracer similar results were obtained (see FIG. 6B). As expected, the FcRc was more effective in inhibiting binding of $^{125}I$ FcRc to the immobilized IgG than in inhibiting $^{125}I$ PA. By contrast, protein A demonstrates equivalent inhibition with both tracers, suggesting that its affinity for the Fc-region of human IgG is higher than that of the FcRc. In similar comparative binding assays using immobilized rabbit or goat IgG in place of human IgG, no heterogeneity in binding was observed within any of the affinity purified FcRc fractions. These findings support the conclusion that the charge and size heterogeneity of the affinity purified FcRc preparation could be attributed to covalently linked cell wall constituents attached to a single type of receptor. Consequently, in the following tests the activity of the total FcRc preparation is compared to protein A.

Antigenic Relationship of Protein A and FcRc

Polyclonal antibodies to protein A or to the major charge species of FcRc were prepared in chicken as described above. Each antibody was tested for its ability to prevent binding of labeled $^{125}I$ PA or $^{125}I$ FcRc to immobilized human IgG. In this assay labeled tracer and immobilized human IgG were incubated for one hour at 37° C. with dilutions of serum containing antibody to protein A, serum containing antibody to FcRc or normal chicken serum. The quantity of radiolabel associated with the immobilized IgG was quantified after washing to remove soluble antigen-antibody complexes containing the labeled tracer Inhibition detected in this assay requires that the antibody will combine with a site on the Fc-receptor that will sterically inhibit its interaction with the corresponding binding site on IgG. The results presented in FIG. 7 indicates that the binding of protein A or FcRc was only inhibited when the corresponding antibody was used. There was no evidence of any antigenic cross-reactivity between those two bacterial Fc-receptors Neither protein A nor the FcRc reacted with any component in normal chicken serum.

Comparison of Species Reactivity of Protein A and FcRc

Using the competitive binding assay described above the ability of different species of IgG to inhibit binding of $^{125}I$ PA or $^{125}I$ FcRc to immobilized human IgG were compared. The results are set forth in FIG. 8 and Table 2 and demonstrate a number of clear differences in binding of the two Fc-receptors. In particular, sheep, cow and goat IgG were much more reactive with the FcRc than with protein A (FIG. 3). Under the assay conditions used, similar inhibition was observed using rabbit IgG. However, protein A was more efficient in its reactivity with human IgG than the FcRc. An absolute comparison of reactivities of protein A and FcRc cannot be made since the FcRc preparation is heterogeneous and accurate estimates of the specific activity of $^{125}I$ labeled tracer cannot be made.

TABLE 2

| Inhibition of Binding to $^{125}I$—PA or $^{125}I$—FcRc to Immobilized Human IgG by IgG from Different Species | | |
|---|---|---|
| | Nanograms IgG Required to Inhibit by 50% | |
| Species | $^{125}I$—FcRc | $^{125}I$—PA |
| Rabbit | 125 | 130 |
| Human | 44 | 13 |

TABLE 2-continued

Inhibition of Binding to $^{125}$I—PA or $^{125}$I—FcRc to Immobilized Human IgG by IgG from Different Species

| Species | Nanograms IgG Required to Inhibit by 50% | |
|---|---|---|
| | $^{125}$I—FcRc | $^{125}$I—PA |
| Pig | 70 | 118 |
| Goat | 180 | 13,000 |
| Sheep | 240 | 40,000 |
| Cow | 405 | 21,000 |
| Dog | 13,000 | 100 |
| Rat | $>10^5$ | $>10^5$ |

The reactivity of human IgG subclasses were also compared in similar experiments. The results presented in FIG. 9 demonstrate a number of interesting reactivities. The labeled FcRc reacted with all four human subclasses with $IgG_3$ and $IgG_1$ showing approximately equivalent reactivity while $IgG_2$ and $IgG_4$ demonstrate lower reactivity. There was considerable variability between the two myeloma proteins of each subclass tested. It is not clear where these differences relate to unique receptors on immunoglobulins from different individuals, e.g., allotypic sites [Schalen et al, Ph.D. Thesis, University of Lund (1982); Haake, J. Immunol. 129:190 (1982)] reactions within Fab regions [Inganas, Scand J. Immunol. 13:343 (1981)], or differences in amino acid compositions of myeloma proteins within the site where the bacterial receptor binds [Shimizu et al, Molec. Immunol. 20:241 (1983)].

Protein A reacted most efficiently with $IgG_1$ and $IgG_4$ and with a lower efficiency with $IgG_2$. The reactivity of two purified $IgG_3$ preparations isolated from myeloma serum showed two distinct reactivities. One $IgG_3$ preparation failed to react with protein A ($IgG_3$ λ#0381), while a second preparation of $IgG_3$ ($IgG_3$ k #0282) showed low but significant reactivity with protein A. These types of differences in $IgG_3$ reactivities with protein A have previously been reported and can be related to the allotype of the immunoglobulin molecule. As noted above, a considerable difference in reactivity of the two myeloma proteins of a given subclass were also observed in the reactivity towards protein A, Table 3.

TABLE 3

Inhibition of Binding $^{125}$I—PA or $^{125}$I—FcRc to Immobilized Human IgG by Human Myelomas

| Species | Nanograms IgG Required to Inhibit by 50% | |
|---|---|---|
| | $^{125}$I—FcRc | $^{125}$I—PA |
| $IgG_1$ (k) | 50 | 30 |
| $IgG_1$ (λ) | 165 | 60 |
| $IgG_2$ (k) | 190 | 265 |
| $IgG_2$ (λ) | 465 | 960 |
| $IgG_3$ (k) | 120 | 666 |
| $IgG_3$ (λ) | 70 | none detected |
| $IgG_4$ (k) | 80 | 39 |
| $IgG_4$ (λ) | 580 | 90 |

In the competitive binding studies using $^{125}$I protein A as the tracer, unlabeled FcRc or unlabeled protein A could inhibit the binding of the labeled tracer to immobilized human or rabbit IgG. The shape of the inhibition curves indicate that Protein A was a more efficient inhibitor of binding to either human or rabbit IgG. When the experiments were repeated using $^{125}$I FcRc as tracer, inhibition by unlabeled FcRc was most efficient while Protein A demonstrated similar inhibition against either labeled tracer. It is not possible to make any absolute comparison between the affinity of protein A and FcRc for human IgG because of the size heterogeneity in the affinity purified FcRc preparation and the resulting uncertainty in determining specific activity of the $^{125}$I FcRc tracer molecules. The competitive binding studies shown in FIG. 6 do indicate, however, that the protein A and FcRc bind to either the same site or two distinct sites in close proximity on the Fc region of human IgG.

Despite this similarity in functional activity, protein A and the FcRc demonstrated no common antigenic determinants (FIG. 7). Furthermore, when the reactivity of the two bacterial Fc receptors were tested against a variety of different mammalian IgG preparations a number of marked differences were observed. The FcRc was found to bind much more efficiently than protein A to sheep, cow and goat immunoglobulins (FIG. 8). The reactivity with pig, human or rabbit IgG did not differ by more than 4-fold under the assay conditions used. Difference in reactivity with human subclasses were also observed. The reactivity of protein A with human IgG subclasses revealed an interesting pattern (FIG. 9). In particular, $IgG_3$ isolated from two patients with myeloma gave markedly different results. One sample, an $IgG_3$λ, failed to react with protein A at all while the second sample, an $IgG_3$k, inhibited binding of protein A to immobilized IgG with 50% inhibition being achieved on addition of 666 ng. as noted above. Differences in protein A binding to $IgG_3$ have previously been observed and have been attributed to an allotypic site present on $IgG_3$. It has been shown that the replacement of an arginine by a histidine at residue 435 of the heavy chain in $IgG_3$ generates a site capable of binding protein A [Shimiju et al, supra]. The results of the above examples show that protein A bound $IgG_1$ better than $IgG_2$ and $IgG_4$ (FIG. 9). The FcRc was shown to bind all four subclasses with $IgG_1$ and $IgG_3$ being the most reactive followed by $IgG_4$ and $IgG_2$. Considerable differences were observed between isolated human subclasses from different myeloma sera with either tracer. These differences may reflect non-Fc binding activities of the receptor or may be attributed to differences in purity of the subclass reagents.

The functional reactivities of the soluble FcRc described here corresponds to those described by Myhre et al, supra, as a type III receptor based on their studies using intact bacteria The ability to isolate a streptococcal type III Fc receptor which maintains its functional activity has a number of clear practical implications. First, the radiolabeled or enzyme labeled FcRc can be used as a tracer in a variety of immunoassays. This approach has been used very successfully with protein A and has only been limited by the range of IgG species, isotypes and subclasses with which protein A reacts. The results herein demonstrate that isolated FcRc has an extended range of reactivities beyond those of protein A. In particular, in contrast to protein A, FcRc reacts well with cow, goat and sheep immunoglobulins. Furthermore, the differences in reactivity of protein A and FcRc with human IgG subclasses show that these immobilized bacterial receptors, either alone or in concert, will be useful for affinity purification of these IgG subclasses.

By definition, bacterial Fc receptors are those with an ability to bind to a site within the constant region (Fc) of various classes and subclasses of mammalian IgG. The Fc region of the IgG antibody molecule is associated with the biological effector properties of the molecule while the antigenic recognition elements are located in the two identical Fab portions of the antibody Consequently, the interaction of bacterial Fc receptors with constant region determinants on the heavy chain of IgG does not interfere with the ability of the antibody to recognize its antigen; it is this property that makes these receptors so useful as tracers of antibody-antigen interaction.

Bacterial Fc receptors bind to the Fc region of various antibodies with a high affinity. This binding is just as efficient, and in some cases more efficient, when the antibody is complexed with antigen. Binding of bacterial Fc receptor can occur efficiently in the presence of low concentrations of detergent and in the absence of divalent cations. The ability to radioactively-label Fc receptors to high specific activity without loss of function makes these molecules extremely valuable for use in a variety of immunoassays. A detailed listing of these assays in which bacterial Fc receptors have been used as tracer may be found in reviews by Goding, J. Immunol. Methods, Vol. 20, pp. 241-153 (1978); and Langone, J. Immunol. Methods, Vol. 51, pp. 3-22 (1982).

The Fc receptors of the invention may be utilized in any immunoassay method which involves the ability of an antibody to recognize or react with an antigen or antigenic determinant (epitope) and the detection or assay of the resulting antigen-antibody complex.

The present invention embodies any such immunoassay method wherein such detection or assay involves a reaction of the above described bacterial Fc receptors with mammalian IgG whereby the Fc receptor binds to the Fc region thereof.

Virtually all such immunoassays involve one or more of the following basic approaches:

(1) Detection of antibodies: The first requirement for developing an immunoassay is the preparation of a specific antibody. In monoclonal antibody techniques this requires a method for screening numerous antibody-secreting clones to identify those that produce antibody with the required antigenic specificity. Similar techniques are required to determine the point at which an immunized animal has mounted a strong specific immune response to a given antigen. Detection of either polyclonal or monoclonal antibodies requires a method of assaying antibody in antigen-antibody complexes. The bacterial Fc receptors of the present invention can be efficiently used for this purpose. In these assays, antibody is allowed to form a complex with immobilized antigen and the excess antibody is then washed away. The antibody in the antigen-antibody complex can then be readily detected by first adding radiolabeled Fc receptor and, after washing, determining the amount of radioactive tracer than remains bound. For these assays, immobilized antigen can be obtained by passive adsorption to plastic surfaces, by covalent attachment to appropriate beads or cells, or by the use of appropriate antigens naturally expressed on cell membranes.

Techniques which employ labeled Fc receptors to detect antigen-antibody complexes are more sensitive and exhibit lower background than methods using labeled second antibodies or Clq. The only limitations of this approach is that the antibodies used must be from a species and of a subclass that reacts with bacterial Fc receptor Currently, with the exception of rat and avian immunoglobulins, antibody production in most species can be followed using the Fc receptor of the present invention. Enzyme-labeled or fluorescent-labeled Fc receptor can also be used for these assays.

A modification of the above procedure in which immobilized Fc receptor is utilized to detect antigen-antibody complexes makes it possible to screen for specific antibodies. In this procedure the immobilized receptor is incubated with the antibody-containing sample, washed free of unbound antibody and then incubated with labeled antigen. The ability to bind the particular labeled antigen to the immobilized Fc receptor-antibody complex can be used to detect the presence of specific antibodies. This technique is only semiquantitative and requires that a purified homogeneous antigen is available.

(2) Competitive binding assay to quantify antigen: Once selected, specific antibodies can be used to develop rapid competitive-binding radioimmunoassays. The first stage in this type of assay is to immobilize the antigen onto a suitable solid phase support. Provided the antibody is specific, preparations rich in antigen but not completely purified are quite satisfactory. The antigen can be immobilized by passive adsorption onto a suitable plastic surface or by selective chemical coupling to an insoluble particle, e.g., Immunobeads (Bio-Rad). The ability of free soluble antigen to competitively inhibit the binding of antibody to the immobilized antigen can then be used as a method for quantifying the amount of antigen in any sample. In this assay the quantity of antibody bound to the immobilized antigen is measured by the binding of labeled Fc receptor. By comparing the percent inhibition of binding of antibody caused by an aliquot of an unknown sample to that caused by an aliquot of a known antigen preparation, under identical assay conditions, it is possible to measure the absolute concentration of specific antigen in any sample.

Antibody prepared against synthetic peptides can be used in conjunction with this technique to detect epitopes on larger proteins. It is known that antibodies can be raised against small synthetic peptides and that these antibodies will recognize antigenic determinants in intact full-sized proteins. This approach has been extended to prepare antibody to synthetic peptides encoded by nucleotide sequences within open reading frames for which a gene product has not yet been identified. Using the specific antibody thus generated and the immobilized synthetic peptide antigen, it is then possible to screen extracts for the presence of a specific protein containing that antigenic structure. Once an extract is found to contain a competing activity, the protein which bears the epitope can be isolated using the competitive binding assay to monitor purification. These approaches have broad applications for detecting a variety of gene products, in particular those coded for by oncogenes.

The possibilities of non-specific inhibition and of inhibition by antigenically related but non-identical molecules apply to all immunoassays regardless of the tracer used.

(3) Detection of specific antigens by Western blotting techniques: The Western blot technique can be used to follow specific epitopes during protein purification. Samples are electrophoresed on SDS or neutral polyacrylamide gels, and proteins are transferred by electroblotting onto a nitrocellulose membrane. The nitrocellulose is reacted with buffer containing a non-reactive protein, e.g., gelatin, to block any unoccupied, non-specific protein binding sites and is then incubated with specific antibody. After a sufficient period of incubation to allow the formation of antigen-antibody complexes, unbound antibody is removed by washing the blot, which is then incubated with labeled Fc receptor for about 1 hour at 37 °C., and, finally, washed free of unbound receptor. The quantity and position of the label remaining bound to the antigen-antibody complex is autoradiographically detected by exposure to x-ray film. Alternatively, enzyme-labeled Fc receptor can be used to identify the position of the antigen-antibody complexes on the blot.

(4) Use of immobilized Fc receptors for the isolation of IgG and IgG subclasses: The ability of immobilized bacterial Fc receptors to interact with free IgG has proven extremely valuable for identifying and isolating a variety of mammalian IgG classes and subclasses. Serum is passed through a column of immobilized Fc receptor and the reactive IgG subclasses bind to the column. This bound IgG can be recovered by elution procedures involving either a change in pH, a change in ionic strength or the use of a chaotrophic agent. Different elution using a pH gradient, for example, can resolve the Fc receptor-bound antibodies into differing subclasses with some species. The use of immobilized Fc receptor is of great value for: (1) isolating IgG from the cell-culture supernatants of hybridoma clones, (2) separating an antigen-antibody complex from free, soluble antigen, and (3) depleting serum of IgG for use in a variety of diagnostic assays.

These products have proven extremely efficient for isolating or eliminating a variety of subclasses of IgG with high binding affinity for the bacterial receptors. Antibodies that have been purified by affinity chromatography on immobilized Fc receptor columns are very effective for use in immunoassays in which the Fc receptor is used as tracer.

The components in a product of the above described methods to be assayed may be coupled or bonded to any assayable ligand such as a radioisotope, fluorescent tag, bio-assayable enzyme, electron dense tag, etc. Those skilled in the art, having been exposed to the principles of the present invention, will be cognizant of the types of assayable ligands and methods for coupling them to the components of the methods of the present invention without the exercise of undue experimentation or inventive faculties.

DESCRIPTION OF THE DRAWINGS

FIG. 9 is a graphic illustration of the inhibition of binding of $^{125}$I-PA or $^{125}$I-FcRc to immobilized human IgG by human IgG subclass standards $IgG_1$ (A), $IgG_2$ (B), $IgG_3$ (C), or $IgG_4$ (D). Reactivity of individual subclass standards, k light chains, with $^{125}$I-FcRc: (●—●); reactivity of individual subclass standards, k light chains, with $^{125}$I-PA: (○---○); reactivity of individual subclass standards, λ light chains, with $^{125}$I-FcRc: (■—■); and reactivity of individual subclass standards, λ light chains, with $^{125}$I-PA: (□---□).

Figure 1:
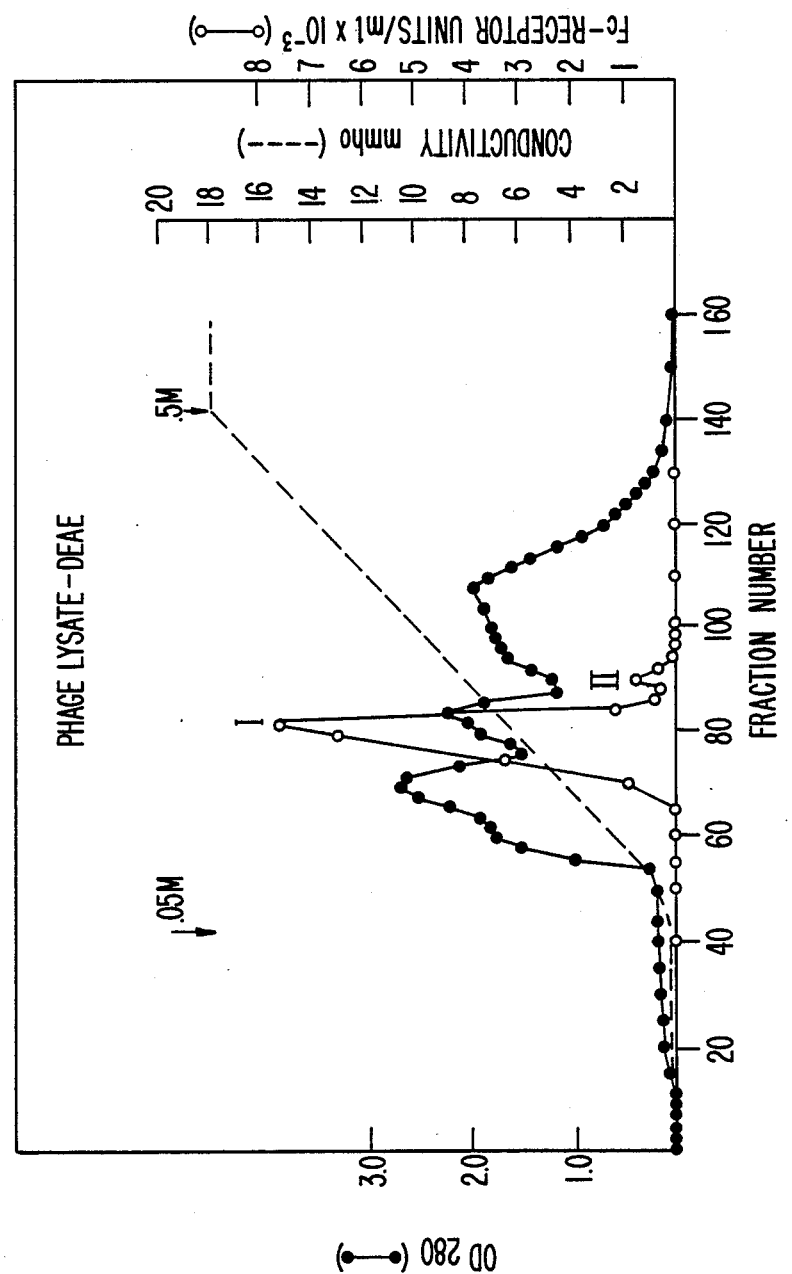
FIG. 1 is a graphic illustration of the results of ion exchange chromatography of phage lysate recovered from the pass through of a cellulose phosphate column. 50 ml containing Fc receptor activity was applied to a 2.5×20 cm DEAE column, equilibrated in 0.015M NaCl, pH 7.2 and eluted with a linear salt gradient from 0.05M to 0.5M. 5 ml fractions were collected. Fc receptor activity:(○—○), $OD_{280}$:(●—●); conductivity:(---).
Figure 2:
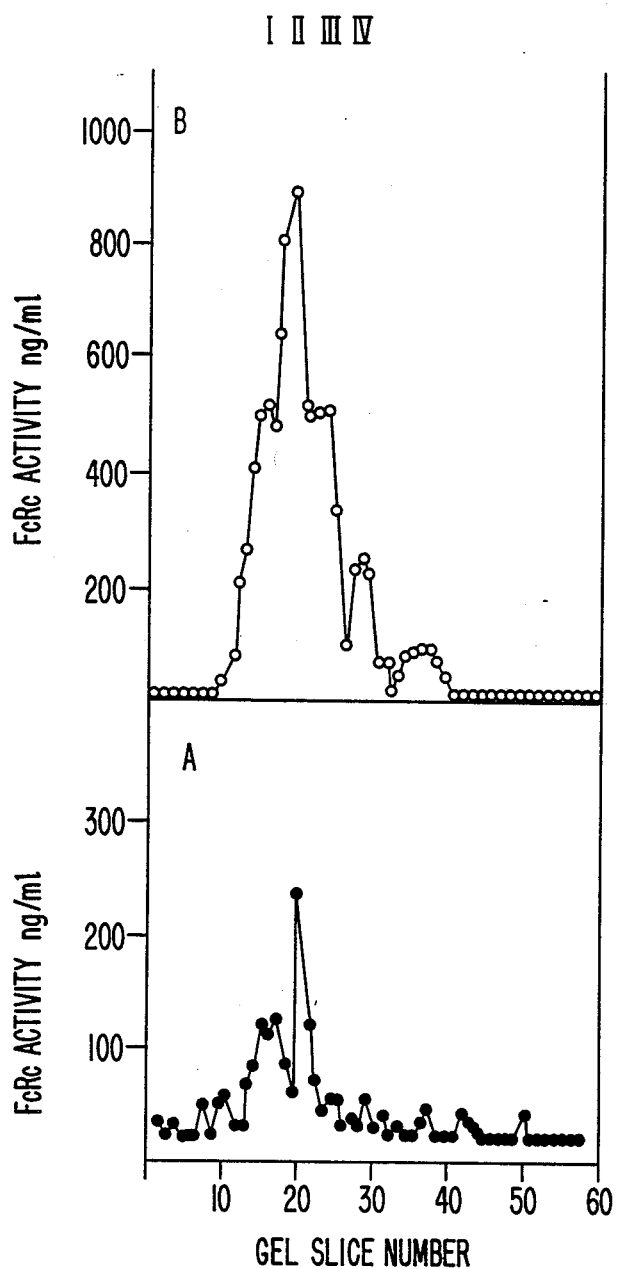
FIG. 2 is a graphic illustration of the results of nondenaturing polyacrylamide gel electrophoresis of affinity purified FcRc and phage lysate containing FcRc.
(A) Functional FcRc activity in crude phage lysate following electrophoresis and elution of gel slices into VBS-gel for 72 hrs.
(B) Affinity purified FcRc, 30 μg, was applied to parallel gels. The functional activity of eluted gel slices is compared with a gel stained with Coomassie blue.
Figure 3:
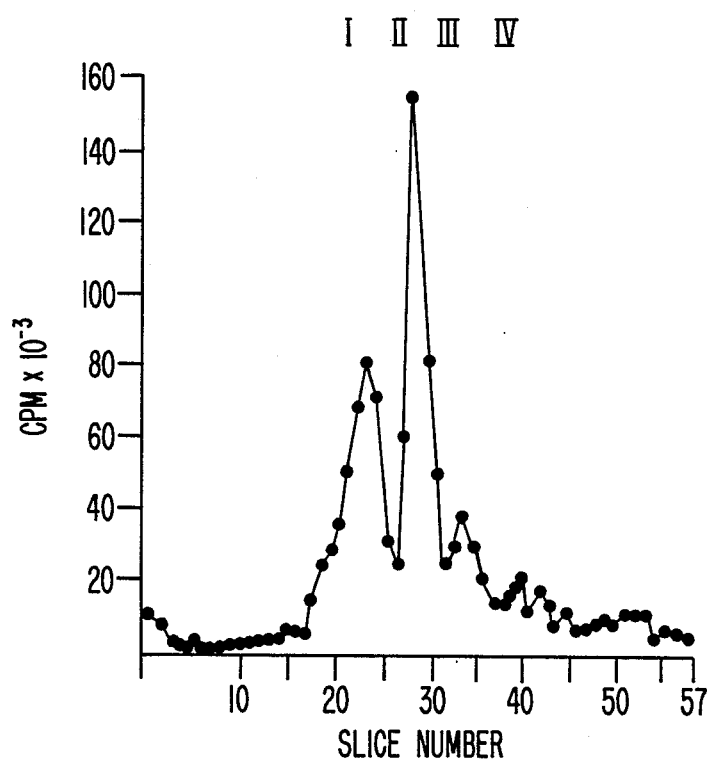
FIG. 3 is a graphic illustration of the results of nondenaturing polyacrylamide gel electrophoresis of affinity purified unlabeled FcRc (30 μg) and $^{125}$I-labeled FcRc (2×10$^6$ cpm)
Figure 5:
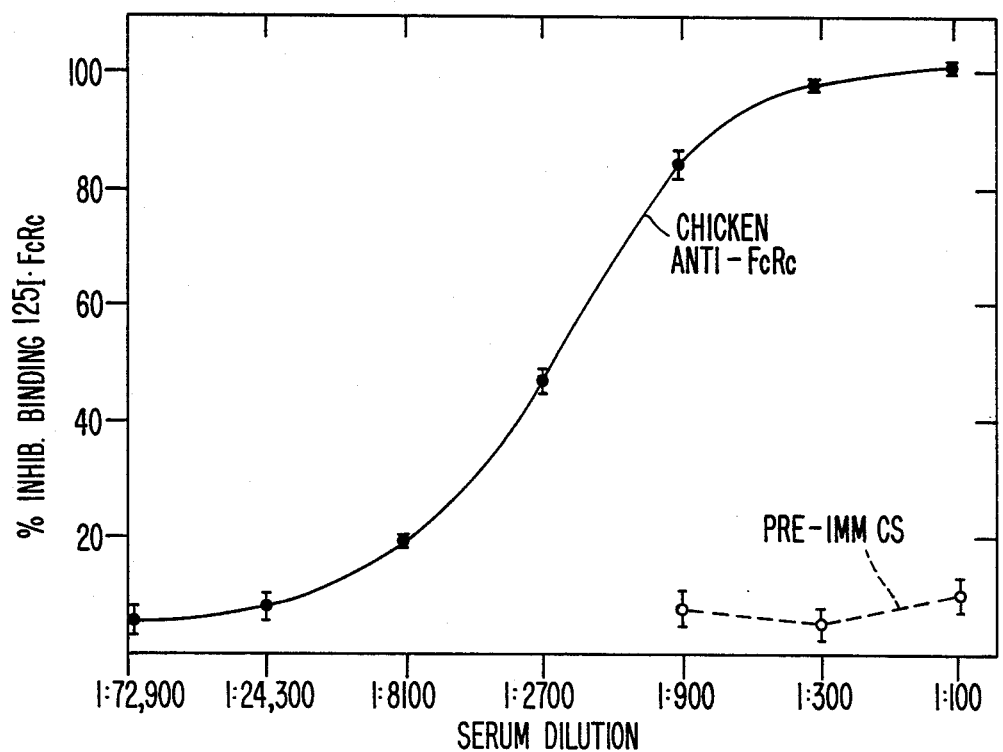
FIG. 5 is a graphic illustration of the results of inhibition of binding of affinity purified unfractionated $^{125}$I-FcRc to immobilized human IgG by chicken antibody prepared against the major charge species (peak II) in the FcRc preparation. Chicken anti-FcRc: (●—●), pre-immune chicken serum: (○---○).
Figure 4:
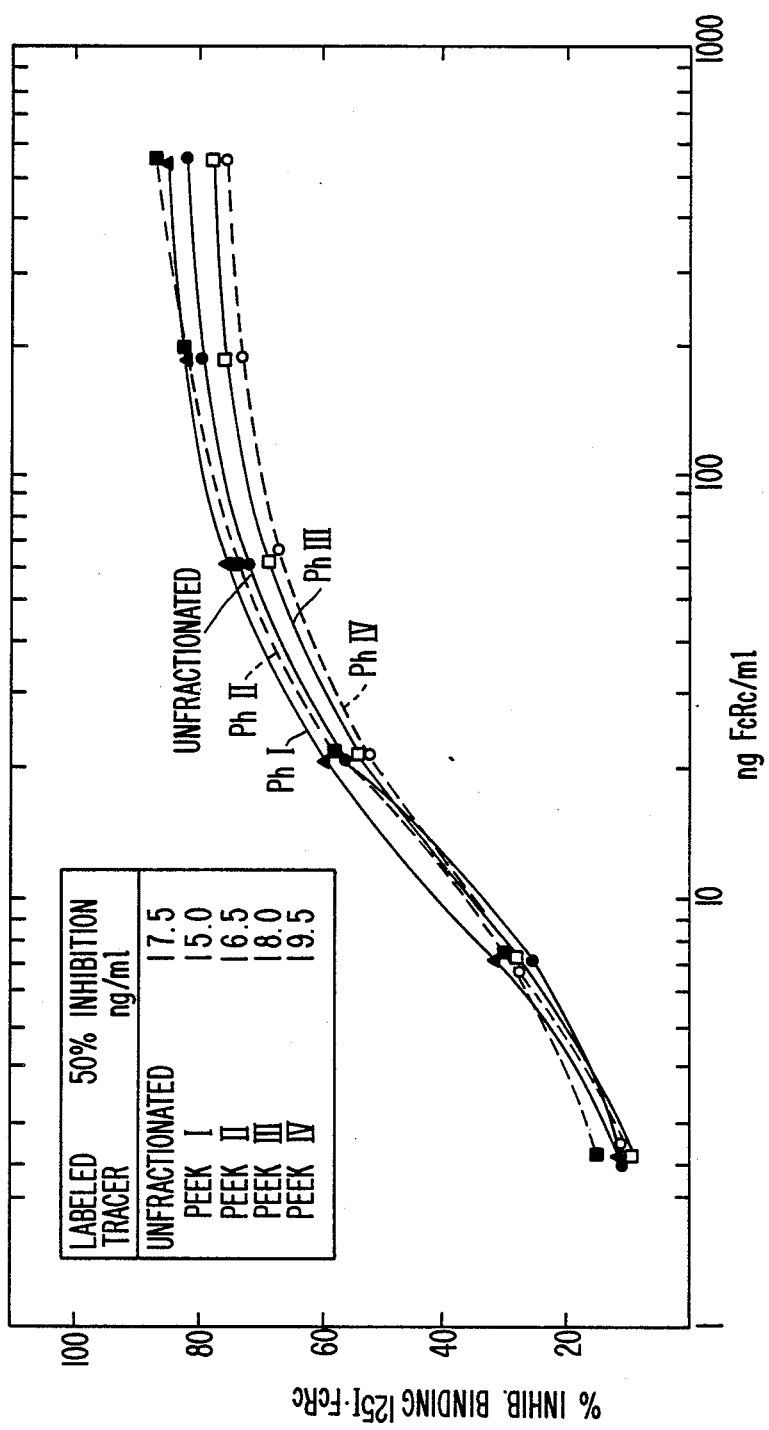
FIG. 4 is a graphic illustration of the results of inhibition of binding of $^{125}$I-affinity purified FcRc and its components to immobilized human IgG by unlabeled, unfractionated FcRc. Individual peaks of $^{125}$I-FcRc correspond to the four major charge species eluted from nondenaturing polyacrylamide gels. $^{125}$I-FcRc, unfractionated:(●—●), and fractions eluted from nondenaturing gels, $^{125}$I-FcRc peak I:
(▲—▲), $^{125}$I-FcRc peak II: (■—■), $^{125}$I-FcRc peak III:(□—□), $^{125}$I-FcRc peak IV (○---○).
Figure 6:
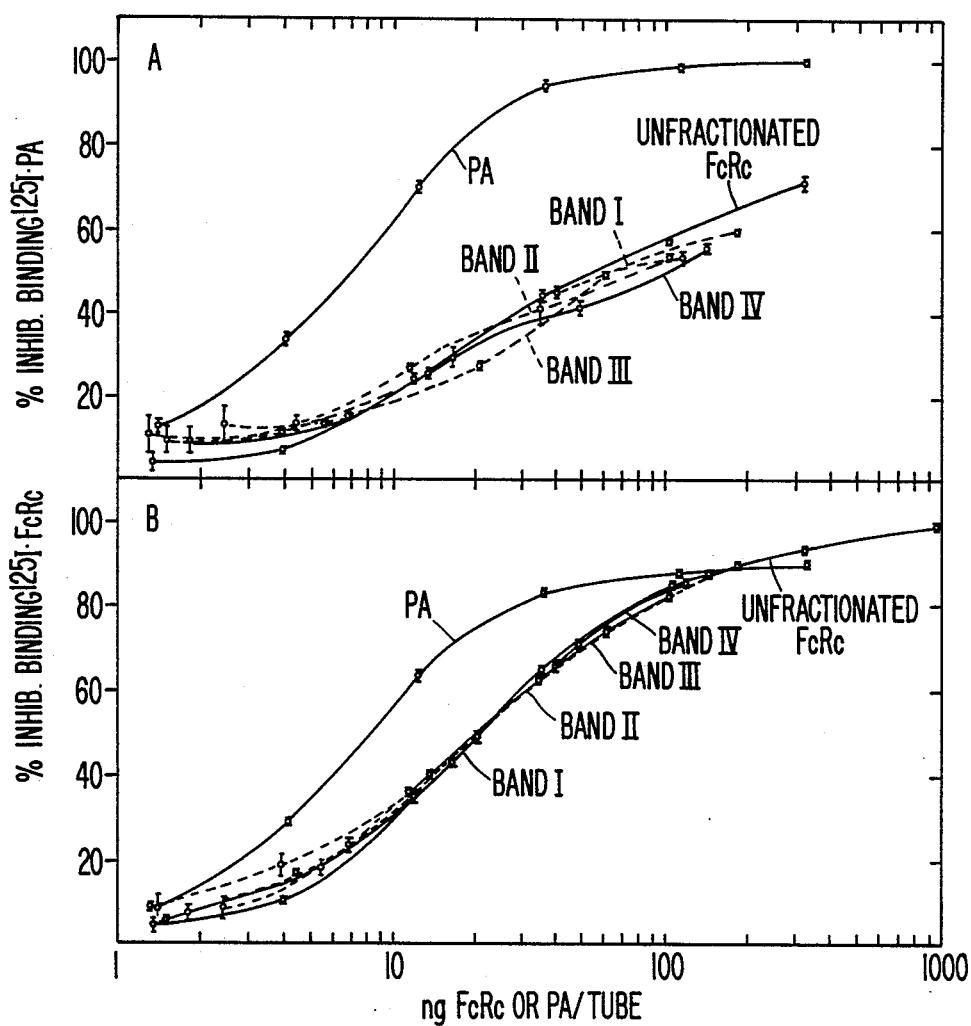
FIG. 6 is a graphic illustration of the inhibition of binding of (A) $^{125}$I-PA or (B) $^{125}$I-FcRc to immobilized human IgG by unlabeled PA, affinity purified unfractionated FcRc or the major FcRc charge species.
Figure 7:
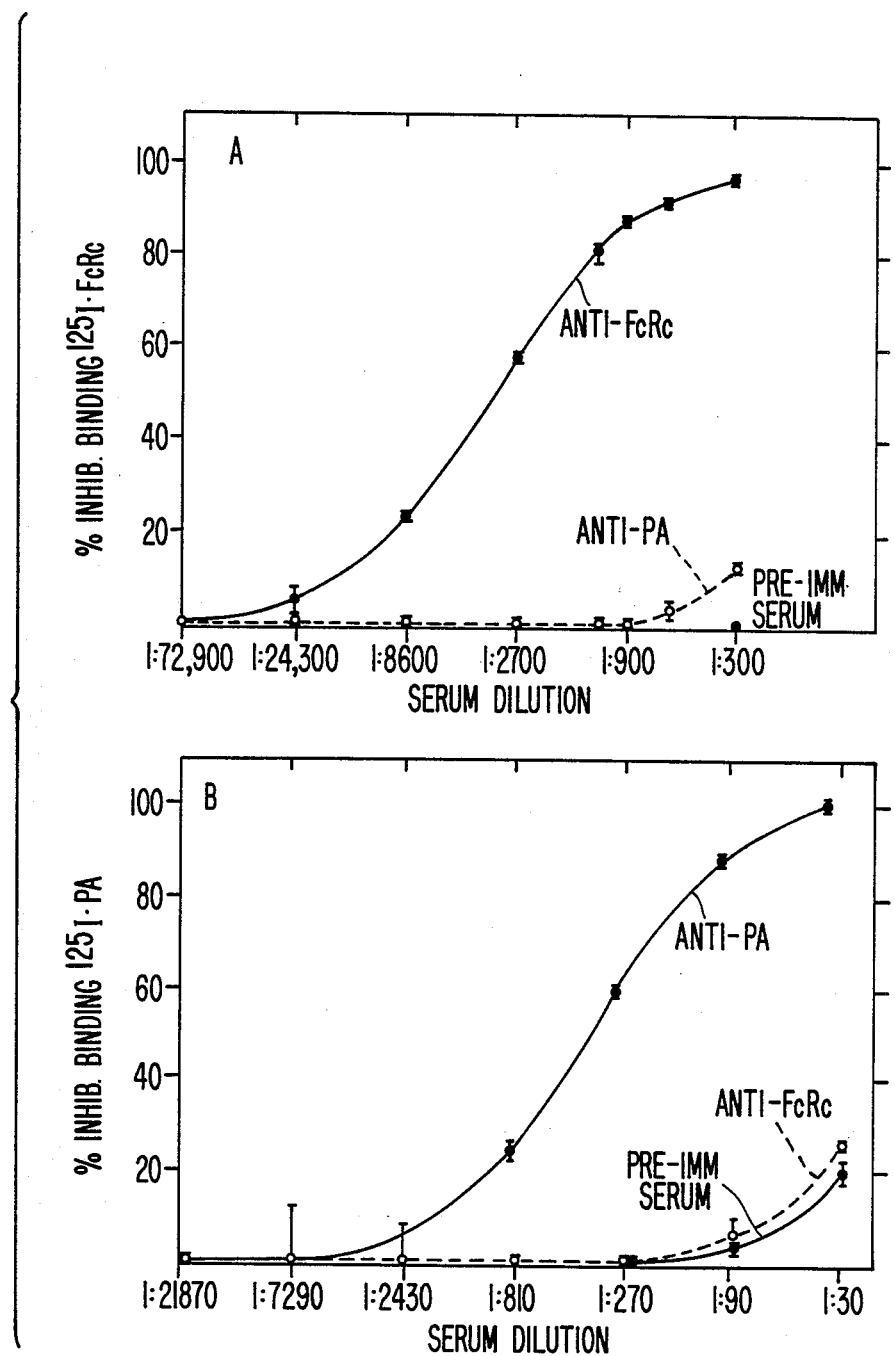
FIG. 7 is a graphic illustration of the inhibition of binding of (A) $^{125}$I-FcRc or (B) $^{125}$I-PA to immobilized human IgG by antibody against the major charge species of FcRc or against PA. (A) anti-FcRc: (———), anti-PA: (○---○) pre-immune chicken serum : (●—●); (B) anti-PA (———), anti-FcRc: (○---○), pre-immune chicken serum (●—●).
Figure 8:
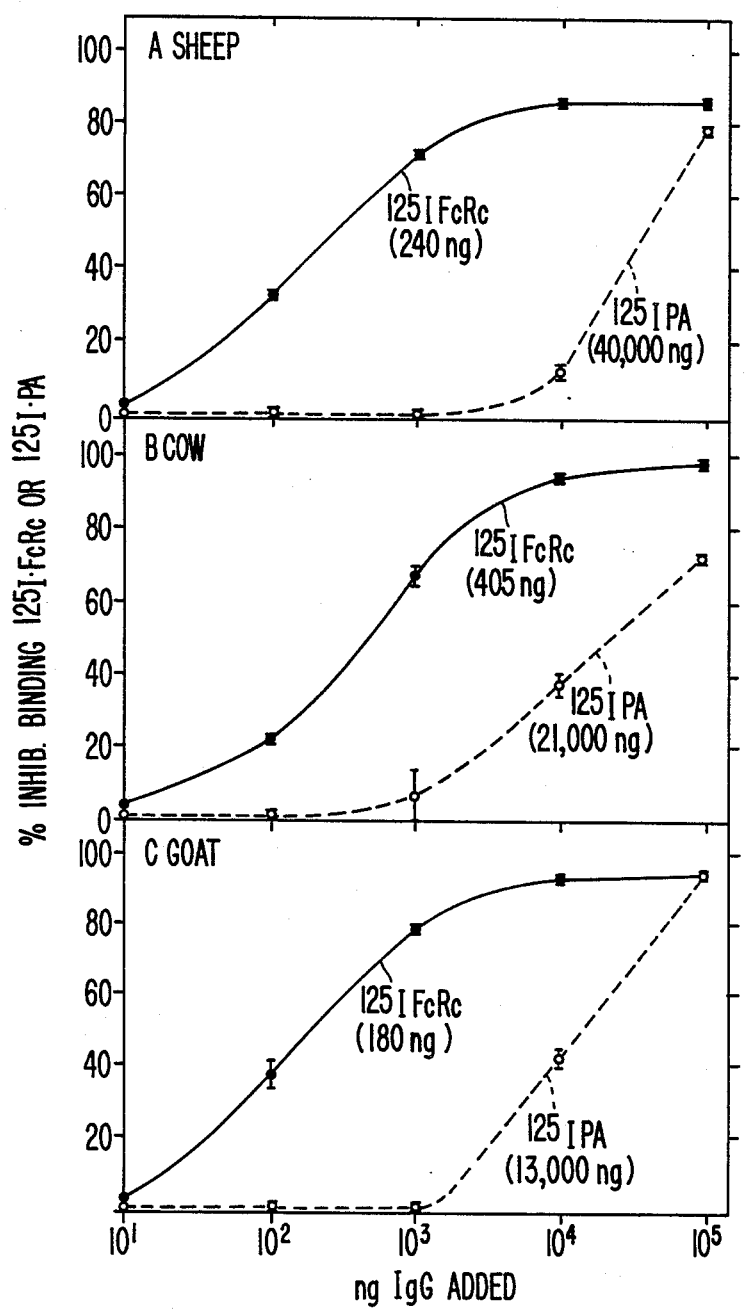
FIG. 8 is a graphic illustration of the inhibition of binding of $^{125}$I-FcRc or $^{125}$I-PA to immobilized human IgG by sheep (A), cow (B), or goat (C) IgG. $^{125}$I-FcRc: (●—●), $^{125}$I-PA (○---○). The numbers in parentheses represent the concentration of IgG required to inhibit by 50% the binding of the labeled tracer to immobilized human IgG.

This invention resulted from research supported by the following grants: No. A1 20665 from the National Institutes of Health; No. BSRG 507 RR 05362-20 from the National Institutes of Health, and National Institutes of Health Training Grant No. 5-T32-A-107110.

The disclosures of each of the references and publications cited herein are incorporated herein by reference.

We claim:

1. In an immunoassay method wherein a bacterial Fc receptor is reacted with a mammalian IgG to bind to a site within the Fc region thereof, the improvement wherein said bacterial Fc receptor is a proteinaceous, antigenic factor derived from a group C streptococcus which is a receptor for the Fc region of IgG and which exhibits four major diffuse protein bands on polyacrylamide gel electrophoresis having apparent molecular weights of 48,000 (band I), 64,000 (band II), 90,000 (band III) and 110,000 (band IV) daltons, respectively.

2. The method of claim 1 further characterized in that band I comprises about 22%, band II comprises about 26%, band III comprises about 11% and band IV comprises about 8% of the total Fc binding activity isolated from group C streptococcus.

3. The method of claim 1 wherein said Fc receptor is derived from the group C streptococcal strain designated 26RP66.

4. In an immunoassay method wherein a bacterial Fc receptor is reacted with a mmalian IGg to bind to a site within the Fc region thereof, the improvement wherein said Fc receptor is a homogenous proteinaceous, antigenic factor derived from a group C streptococcus which is a receptor for the Fc region of IGg and which exhibits one major diffuse protein band on polyacrylamide gel electrophoresis and has an apparent molecular weight of 30,000 daltons.

5. The method of claim 4 wherein said Fc receptor is streptococcal strain designated 26RP66.

6. The method of claim 1 for assaying mammalian IgG in a sample wherein said IgG in said sample is allowed to form an IgG/antigen complex with antigen immobilized on an inert substrate, reacting said immobilized IgG/antigen complex with said bacterial Fc receptor which has been previously labeled with an assayable ligand whereby said labeled Fc receptor binds to the Fc region of said complexed IgG and assaying said labeled ligand in said antigen/IgG/Fc receptor complex.

7. The method of claim 6 wherein said bacterial Fc receptor is labeled with a radioisotope, enzyme or electron dense ligand.

8. The method of claim 1 for assaying mammalian IgG in a sample wherein said IgG in said sample is allowed to react with said bacterial Fc receptor immobilized on an inert substrate whereby said Fc receptor binds to the Fc region of said IgG, allowing said IgG/Fc receptor reaction product to form an Fc receptor/IgG/antigen complex with an antigen which has been previously labeled with an assayable ligand and or assaying said labeled ligand in said antigen/IgG/Fc receptor complex.

9. The method of claim 8 wherein said antigen is labeled with a radioisotope, enzyme or electron dense ligand.

10. The method of claim 1 for the competitive-binding immunoassay of an antigen in a sample wherein the percent inhibition of binding of IgG to antigen immobilized on an inert substrate by a known quantity of free antigen is compared with the percent inhibition of binding of IgG to said antigen immobilized on said inert substrate by the unknown quantity of free anrigen in said sample to quantify the concentration of antigen in said sample wherein the degree of binding of IgG to said immobilized antigens is determined by reaction of the Fc region of the immobilized antigen/IgG complex with said bacterial Fc receptor labeled with an assayable ligand and assaying said labeled ligand in said antigen/IgG/Fc receptor complex.

11. The method of claim 10 wherein said bacterial Fc receptor is labeled with a radioisotope, enzyme or electron dense ligand.

12. The method of claim 1 for the direction of an antigen by the Western blotting technique wherein a sample containing antigen is electrophoresed and proteins separated thereby are transferred by electroblotting onto a membrane, said membrane is reacted with a protein to block any unoccupied, non-specific protein binding sites thereon, said membrane is reacted with IgG to form antigen/IgG complexes on said membrane, reacting said antigen/IgG complexes with said bacterial Fc receptor labeled with an assayable ligand whereby said labeled Fc receptor binds to the Fc region of said antigen/IgG complex and assaying said labeled ligand in said antigen/IgG/Fc receptor complex on said membrane.

13. The method of claim 12 wherein said bacterial Fc receptor is labeled with a radioisotope, enzyme or electron dense ligand.

14. The method of claim 1 for assaying mammalian IgG wherein a sample containing said IgG is allowed to react with said bacterial Fc receptor immobilized on an inert substrate whereby said Fc receptor binds to the Fc region of said IgG.

15. The method of claim 14 including the step of subsequently separating said bound IgG from said immobilized Fc receptor.

16. Purified proteinaceous, antigenic factor derived from a group C streptococcus which is a receptor for the Fc region of IgG and which exhibits four major diffuse protein bands on polyacrylamide gel electrophoresis having apparent molecular weights of 48,000 (band I), 64,000 (band II), 90,000 (band III) and 110,000 (band IV) daltons, respectively.

17. The factor of claim 16 further characterized in that band I comprises about 22%, band II comprises about 26%, band III comprises about 11% and band IV comprises about 8% of the total Fc binding activity isolated from group C streptococcus.

18. The factor of claim 16 derived from the group C streptococcal strain designated 26RP66.

19. A homogeneous, proteinaceous, antigenic factor derived from a group C streptococcus which is a receptor for the Fc region of IgG and which exhibits one major diffuse protein band on polyacrylamide gel electrophoresis and has an apparent molecular weight of 30,000 daltons.

20. The factor of claim 16 or 19 labeled with a radioisotope, enzyme, or electron dense ligand.

21. The labeled factor of claim 20 wherein said radioisotope is $^{125}$I, $^{131}$I, $^{3}$H, $^{14}$C or $^{35}$S.

22. The labeled factor of claim 20 wherein said enzyme is lactoperoxidase, horse-radish peroxidase, alkaline phosphatase, or glucose oxidase.

23. The labeled factor of claim 20 wherein said electron dense ligand is ferritin, gold or horse-radish peroxidase.

24. The factor of claim 16 or 19 immobilized to an inert support.

* * * * *

UNITED STATES PATENT AND TRADEMARK OFFICE
CERTIFICATE OF CORRECTION

PATENT NO. : 4,900,660
DATED : February 13, 1990
INVENTOR(S) : Michael D.P. BOYLE, ET AL It is certified that error appears in the above-identified patent and that said Letters Patent is hereby corrected as shown below:

In column 1, line 7, insert the following paragraph:

-- Research leading to the conception and reduction to practice of the invention claimed herein was supported in part by Grant Nos. AI-20665, BSRG-S07-RR05362-20 and 5-T32-AI07110 issued by the National Institutes of Health. The United States Government has certain rights in and to the claimed invention. --

Signed and Sealed this

Fourth Day of April, 1995

Attest:

BRUCE LEHMAN

Attesting Officer   Commissioner of Patents and Trademarks